US011534335B2

(12) United States Patent
Gonzales et al.

(10) Patent No.: US 11,534,335 B2
(45) Date of Patent: Dec. 27, 2022

(54) APPARATUS AND METHODS FOR TREATMENT OF OBSTRUCTIVE SLEEP APNEA UTILIZING CRYOLYSIS OF ADIPOSE TISSUES

(71) Applicant: CRYOSA, INC., Shoreview, MN (US)

(72) Inventors: Donald A. Gonzales, Austin, TX (US); Mitchell Elliott Levinson, Pleasanton, CA (US)

(73) Assignee: Cryosa, Inc., Arden Hills, MN (US)

( * ) Notice: Subject to any disclaimer, the term of this patent is extended or adjusted under 35 U.S.C. 154(b) by 1553 days.

(21) Appl. No.: 15/510,879

(22) PCT Filed: Sep. 24, 2015

(86) PCT No.: PCT/US2015/051903
§ 371 (c)(1),
(2) Date: Mar. 13, 2017

(87) PCT Pub. No.: WO2016/053741
PCT Pub. Date: Apr. 7, 2016

(65) Prior Publication Data
US 2017/0246032 A1 Aug. 31, 2017

Related U.S. Application Data (60) Provisional application No. 62/058,616, filed on Oct. 1, 2014.

(51) Int. Cl.
*A61F 7/12* (2006.01)
*A61B 18/02* (2006.01)
(Continued)

(52) U.S. Cl.
CPC .............. *A61F 7/12* (2013.01); *A61B 18/02* (2013.01); *A61F 5/566* (2013.01); *A61F 7/123* (2013.01);
(Continued)

(58) Field of Classification Search
CPC .. A61F 7/12; A61F 7/123; A61F 5/566; A61F 2007/0017; A61F 2007/0026;
(Continued)

(56) References Cited

U.S. PATENT DOCUMENTS

| 3,712,306 A | 1/1973 | Bryne |
| 5,245,023 A | 9/1993 | Peoples et al. |

(Continued)

FOREIGN PATENT DOCUMENTS

| JP | H01-223961 A | 9/1989 |
| WO | WO97/44092 A1 | 11/1997 |

(Continued)

OTHER PUBLICATIONS

Avram et al., Cryolipolysis for Subcutaneous Fat Layer Reduction, Lasers in Surgery and Medicine, 41: 703-708; Dec. 2009.

(Continued)

*Primary Examiner* — Eun Hwa Kim
*Assistant Examiner* — Catherine Premraj
(74) *Attorney, Agent, or Firm* — Shay Glenn LLP (57) ABSTRACT

A heat exchanger is disclosed for causing cryolysis of adipose tissue of a human tongue. The heat exchanger includes a body having cooling channels for circulating fluids therein. The body forms a contact surface that contacts a portion of the dorsal surface of the tongue and a portion of the base of the tongue. The heat exchanger includes a pair of side walls extending from the body and forming a pair of side contact surfaces that are dimensioned so that they contact the dorsal and lateral surfaces of the tongue in a manner so as to constrict the tongue when the contact surface is in contact with the tongue. A method of treatment for apnea using the heat exchanger and/or administering a chemical adipolysis formulation/vasoconstriction agent is also disclosed.

26 Claims, 9 Drawing Sheets

(51) Int. Cl.
- *A61F 5/56* (2006.01)
- *A61B 18/00* (2006.01)
- *A61F 7/00* (2006.01)

(52) U.S. Cl.
CPC ............. *A61B 2018/0022* (2013.01); *A61B 2018/00291* (2013.01); *A61B 2018/00327* (2013.01); *A61B 2018/00642* (2013.01); *A61B 2018/00714* (2013.01); *A61B 2018/00744* (2013.01); *A61B 2018/00791* (2013.01); *A61B 2018/00815* (2013.01); *A61B 2018/00821* (2013.01); *A61B 2018/0262* (2013.01); *A61F 2007/0017* (2013.01); *A61F 2007/0056* (2013.01); *A61F 2007/0087* (2013.01); *A61F 2007/0096* (2013.01)

(58) Field of Classification Search
CPC ..... A61F 2007/0087; A61F 2007/0096; A61B 18/02; A61B 2018/0022; A61B 2018/00291; A61B 2018/00327; A61B 2018/00642; A61B 2018/00714; A61B 2018/00744; A61B 2018/00791; A61B 2018/00815; A61B 2018/00821; A61B 2018/0262

See application file for complete search history.

(56) References Cited

U.S. PATENT DOCUMENTS

| | | |
|---|---|---|
| 5,534,432 A | 7/1996 | Peoples et al. |
| 5,800,379 A | 9/1998 | Edwards |
| 6,017,337 A | 1/2000 | Pira |
| 6,032,675 A | 3/2000 | Rubinsky |
| 6,041,787 A | 3/2000 | Rubinsky |
| 6,045,549 A | 4/2000 | Smethers et al. |
| 6,126,657 A | 10/2000 | Edwards et al. |
| 6,245,537 B1 | 6/2001 | Williams et al. |
| 6,316,262 B1 | 11/2001 | Huisman et al. |
| 6,378,525 B1 | 4/2002 | Beyar et al. |
| 6,408,851 B1 | 6/2002 | Karell |
| 6,514,515 B1 | 2/2003 | Williams |
| 6,548,569 B1 | 4/2003 | Williams et al. |
| 6,555,123 B2 | 4/2003 | Williams et al. |
| 6,585,994 B2 | 7/2003 | Williams et al. |
| 6,592,892 B1 | 7/2003 | Williams |
| 6,593,116 B1 | 7/2003 | Huisman et al. |
| 6,610,764 B1 | 8/2003 | Martin et al. |
| 6,746,447 B2 | 6/2004 | Davison et al. |
| 6,770,071 B2 | 8/2004 | Woloszko et al. |
| D568,258 S | 5/2008 | Adam |
| 7,367,341 B2 | 5/2008 | Anderson et al. |
| 7,458,932 B2 * | 12/2008 | Sun ............... A61B 1/0008 600/185 |
| 7,507,235 B2 | 3/2009 | Keogh et al. |
| 7,575,870 B1 | 8/2009 | Lalvani et al. |
| 7,842,029 B2 | 11/2010 | Anderson et al. |
| 7,850,683 B2 | 12/2010 | Elkins et al. |
| 7,854,754 B2 | 12/2010 | Ting et al. |
| 8,192,474 B2 | 6/2012 | Levinson |
| 8,275,442 B2 | 9/2012 | Allison |
| 8,285,390 B2 | 10/2012 | Levinson et al. |
| 8,287,579 B2 | 10/2012 | Nimitz |
| 8,523,927 B2 | 9/2013 | Levinson et al. |
| 8,603,073 B2 | 12/2013 | Allison |
| 8,676,338 B2 | 3/2014 | Levinson |
| 8,702,774 B2 | 4/2014 | Baker et al. |
| 8,768,468 B2 | 7/2014 | Garcia et al. |
| 8,840,608 B2 | 9/2014 | Anderson et al. |
| 9,078,634 B2 | 7/2015 | Gonzales et al. |
| 9,439,805 B2 | 9/2016 | Gonzales et al. |
| 9,844,461 B2 | 12/2017 | Levinson et al. |
| 10,111,774 B2 | 10/2018 | Gonzales et al. |
| 11,437,150 B2 | 9/2022 | Rondoni et al. |
| 11,439,532 B2 | 9/2022 | Velis |
| 11,457,971 B2 | 10/2022 | Wolf et al. |
| 2002/0026226 A1 | 2/2002 | Ein |
| 2002/0164729 A1 | 11/2002 | Skral et al. |
| 2003/0220374 A1 | 11/2003 | Needleman |
| 2004/0234576 A1 | 11/2004 | Martin et al. |
| 2005/0133026 A1 | 6/2005 | Seleznev et al. |
| 2006/0235264 A1 | 10/2006 | Vassallo |
| 2007/0129714 A1 | 6/2007 | Elkins et al. |
| 2007/0144539 A1 | 6/2007 | van der Burg et al. |
| 2007/0163603 A1 | 7/2007 | Sikora |
| 2007/0255362 A1 | 11/2007 | Levinson et al. |
| 2007/0270925 A1 | 11/2007 | Levinson |
| 2008/0023012 A1 | 1/2008 | Dineen et al. |
| 2008/0058584 A1 | 3/2008 | Hirotsuka et al. |
| 2008/0066769 A1 | 3/2008 | Dineen et al. |
| 2008/0066864 A1 | 3/2008 | Ballantine et al. |
| 2008/0077201 A1 | 3/2008 | Levinson et al. |
| 2008/0077211 A1 | 3/2008 | Levinson et al. |
| 2008/0083461 A1 | 4/2008 | Viken |
| 2008/0188947 A1 | 8/2008 | Sanders |
| 2008/0200910 A1 | 8/2008 | Bur er et al. |
| 2008/0287839 A1 * | 11/2008 | Rosen ............... A61H 7/008 601/18 |
| 2009/0014012 A1 * | 1/2009 | Sanders ............... A61N 1/05 128/848 |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0107001 A1 | 4/2009 | McCarthy |
| 2009/0118722 A1 | 5/2009 | Ebbers et al. |
| 2009/0120446 A1 | 5/2009 | Vaska et al. |
| 2009/0123886 A1 | 5/2009 | Vaska et al. |
| 2009/0192504 A1 | 7/2009 | Askew |
| 2009/0287060 A1 | 11/2009 | Pell et al. |
| 2010/0057065 A1 | 3/2010 | Krimsky |
| 2011/0155143 A1 * | 6/2011 | Shantha ............... A61F 5/566 128/848 |
| 2011/0166598 A1 | 7/2011 | Gonazles et al. |
| 2011/0224761 A1 | 9/2011 | Manstein |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0197361 A1 * | 8/2012 | Gonzales ............... A61F 7/12 607/105 |
| 2012/0239123 A1 | 9/2012 | Weber et al. |
| 2014/0277219 A1 | 9/2014 | Nanda |
| 2014/0277302 A1 | 9/2014 | Weber et al. |
| 2015/0047301 A1 | 2/2015 | Messersi' |
| 2015/0148791 A1 | 5/2015 | Birdsall et al. |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0251120 A1 | 9/2015 | Jakop |
| 2016/0022345 A1 | 1/2016 | Baust et al. |
| 2016/0051401 A1 | 2/2016 | Yee et al. |
| 2016/0183997 A1 | 6/2016 | Burnett et al. |
| 2016/0354234 A1 | 12/2016 | Dabrowiak |
| 2017/0079833 A1 | 3/2017 | Frangineas et al. |
| 2018/0228646 A1 | 8/2018 | Gonzales et al. |
| 2019/0254867 A1 | 8/2019 | Gonzales et al. |
| 2022/0257272 A1 | 8/2022 | Wolf et al. |
| 2022/0265344 A1 | 8/2022 | Wolf, II et al. |
| 2022/0296887 A1 | 9/2022 | Johnson et al. |

FOREIGN PATENT DOCUMENTS

| | | |
|---|---|---|
| WO | WO99/003411 A1 | 1/1999 |
| WO | WO2003/078596 A2 | 9/2003 |
| WO | WO2008/055243 A2 | 5/2008 |
| WO | WO2009/026471 A1 | 2/2009 |
| WO | WO2010/036732 A1 | 4/2010 |
| WO | WO2010/127315 A2 | 11/2010 |
| WO | WO2011/091293 A1 | 7/2011 |
| WO | WO2011/091431 A1 | 7/2011 |

(56) References Cited

FOREIGN PATENT DOCUMENTS

| WO | WO2012/103242 A1 | 8/2012 |
| WO | WO2012/103315 A2 | 8/2012 |
| WO | WO2016/033384 A1 | 3/2016 |

OTHER PUBLICATIONS

Coleman et al., Clinical Efficacy of Noninvasive Cryolipolysis and Its Effects on Peripheral Nerves, Aesth. Plast. Surg., 33: 482-488; Mar. 2009.
Day et al.; Popsicle Panniculitis; Pediatric Emergency Care; 8(2); 91-93; Apr. 1992.
Epstein et al.; Popsicle Panniculitis; NEJM; 282(17); 966-967; Apr. 23, 1970.
Gage et al.; Critical temperature for skin necrosis in experimental cryosurgery; Cryobiology; 19(3); pp. 273-282; Jun. 1982.
Kim et al.; Tongue fat and its relationship to obstructive sleep apnea; Sleep; 37(10); pp. 1639-1648; Oct. 2014.
MEDICALXPRESS; Study shows that tongue size and fat may predict sleep apnea risk in obese adults; 3 pages retrived from the interenet (https://medicalxpress.com/news/2014-09-tongue-size-fat-apnea-obese.html) on Nov. 27, 2018.
Nelson et al., Cryolipolysis for Reduction of Excess Adipose Tissue; Semin. Cutan. Med. Surg., 28(4): 244-249; Dec. 1, 2009.
Rajkumar et al.; Popsicle Panniculitis of the Cheeks; Clinical Pediatrics.; 15(7); 619-621; Jul. 1976.
Zelickson et al., Cryolipolysis for Noninvasive Fat Cell Destruction: Initial Results from a Pig Model; Dermatol. Surg., 35: 1462-1470; Oct. 2009.

\* cited by examiner

Administer a chemical adipolysis formulation into the tongue

FIG. 13

APPARATUS AND METHODS FOR TREATMENT OF OBSTRUCTIVE SLEEP APNEA UTILIZING CRYOLYSIS OF ADIPOSE TISSUES

CROSS REFERENCE TO RELATED APPLICATIONS

The present application claims priority to U.S. Provisional Application 62/058,616, filed Oct. 1, 2014, the entirety of which is hereby incorporated by reference.

BACKGROUND

Obstructive sleep apnea (OSA) is disease that affects up to 20% of the adult population. OSA generally occurs during sleep when soft tissue obstructs the airway and creates cessation of, or impedes, breathing. Obstruction can occur at one or more levels including the retropalatal and retrolingual areas. Surgical correction of such obstructions remains a challenge, specifically for the retrolingual area. Removal or ablation of tongue tissue has been utilized with poor results due to complications, such as severe bleeding, abscess formation, and/or the inability to move the tongue anterior enough to relieve the obstruction.

It is known that patients with OSA have a higher percentage of adipose deposits in the areas of obstruction, specifically, the soft palate and uvula, base of tongue and lateral pharyngeal walls. The adipose tissue may be up to or greater than 40% of the total volume of tissues in these areas. Removal of the fat deposits in these areas would permit relief from OSA symptoms while preserving surrounding tissue. To date, however, cryolytic treatment of OSA has involved procedures analogous to ablation, merely substituting cryolytic cold for electrolytic heat and nonselectively destroying tissue in a similar manner—and with the same complications.

SUMMARY

The disclosed technology allows for the treatment of apnea by causing adipolysis of subcutaneous adipose tissue of the tongue without damaging the surface tissue. Cold temperature is delivered to the base to the tongue to invoke a cryolytic tissue response that triggers the apoptosis process within the tissue. To this end, the cold temperature is not of sufficient level and duration to cause immediate tissue destruction (often associated with ablation where the cell dies from necrosis—a form of traumatic cell death due to acute cellular injury). Rather, the apoptosis process is a biological response within the natural life cycle of the cell, also referred to as a programmed cell death. The exposure to the cold triggers the apoptosis process which causes the cell to naturally die over a period of time (e.g., over a period of several weeks and/or months), thereby reducing the size of the tissue that may be obstructing the airway.

The disclosed technology enhances the mechanism that cold temperature is delivered to the tongue by reducing blood flow through the tongue during the application of the cold temperature, thereby allowing for several benefits, for example, but not limited to, (i) a shorter treatment time (namely, the application and/or exposure time of the cold temperature by the patient), (ii) a deeper penetration of the cold delivery into the tongue, thereby increasing the effective range and size of the treatment, (iii) a higher treatment temperature (as compared with no constriction of the vascular flow). Additionally, in reducing the blood circulation within the tongue, the thermal load of the tongue is reduced, thereby a smaller heat exchanger can be employed, the smaller apparatus being more comfortable to the patient when employed during the treatment.

The disclosed method further employs pharmacological and/or chemical agents, independently, or in conjunction, with the disclosed technology to treat apnea. The chemical agents may be administered to perform adipolysis. Alternatively, or in addition to, the pharmacological agent may be a vasoconstrictor to reduce the blood circulation.

In one aspect, the present disclosure describes a heat exchanger for causing cryolysis of adipose tissue of a human tongue. The heat exchanger includes a cooling inlet, a cooling outlet, and a body having one or more channels for circulating a heat-transfer fluid therein (e.g., chilled water, refrigerant, and/or water-glycerin solution). The one or more channels connects the cooling inlet and cooling outlet. The body forms a contact surface to cover the base of the tongue in which the body includes (i) a first region having a contact surface (e.g., wherein the contact surface is curved or substantially flat) to contact a portion of the dorsal surface of the tongue and (ii) a second region formed to contact a portion of the base of the tongue, the second region forming a protrusion that extends from the first region and curves over and around the tongue to contact the base of the tongue. The heat exchanger includes a pair of side walls that extends from the body and forms a pair of side contact surfaces. The side walls are dimensioned so that they contact the dorsal and lateral surfaces of the tongue in a manner so as to constrict the tongue when the contact surface is in contact with the tongue.

In some embodiments, the contact surface includes one or more concave recesses, whereby the recesses create a suction force between the interior surface of the concave recess and the corresponding surface of the base of the tongue when the contact surface is in contact with the base of the tongue. In some embodiments, the contact surface is concave (e.g., C-shaped, U-shaped, or V-shaped).

In some embodiments, the first region and the second region are of substantially the same thickness (e.g., less than 10% difference). In some embodiments, the second region is between about 1 and 2 inches in length. The pair of side walls, in some implementations, forms a gap therebetween. The gap, in some embodiments, is between about 1.5 and 2 inches. In some embodiments, the contact surface and the side contact surfaces have a combined surface area between about 4 and 10 square inches.

In some embodiments, the one or more channels form a serpentine pattern that span a substantial portion (e.g., greater than about 50%) of the interior of the body.

In some embodiments, the cooling inlet and the cooling outlet are located at a distal end of the body. In some embodiments, each of the cooling inlet and the cooling outlet comprises a quick-disconnect fitting. In some embodiments, at least one of the cooling inlet and the cooling outlet is angled with respect to the body.

In some embodiments, the heat exchanger further includes a suction inlet located on the contact surface; a suction outlet having a coupling to couple to a hose; and a suction channel connecting the suction inlet and the suction outlet. In some embodiments, the suction outlet is located (i) at the distal end of the body and (ii) proximal to the cooling inlet and cooling outlet.

In some embodiments, the heat exchanger further includes one or more thermal sensors (e.g., thermocouples). At least one of the thermal sensors is located at a location selected from the group consisting of a distal end of the contact surface of the body, the inlet, the outlet, and a proximal end of the contact surface of the body.

In some embodiments, the body comprises a material selected from the group consisting of copper, silver, and aluminum. The body, in some embodiments, includes a top-side exterior surface, said surface being curved to correspond to the oral cavity surface.

In another aspect, the present disclosure describes a method for causing adipolysis of adipose tissue of a human tongue to treat apnea. The method includes applying a heat exchanger so as to contact a portion of the dorsal surface of the tongue and a portion of the base of a tongue. The heat exchanger includes a body having a first region and a second region for contacting the tongue in which the first region has a contact surface (e.g., wherein the contact surface is curved or substantially flat) to contact a portion of the dorsal surface of the tongue, and in which the second region forms a protrusion that extends from the first region and curves over and around the tongue to contact the base of the tongue.

The method further includes constricting the tongue in a manner to create a pressure thereon, whereby the dorsal surface and lateral surface of the tongue is confined by the constriction. The method further includes circulating a heat-transfer fluid through the heat exchanger (e.g., to maintain the contact surface of the heat exchange at a temperature between −15° C. and 0° C., preferably at −10° C.) (e.g., for a pre-defined treatment time, e.g., between 10 minutes and 2 hours).

In some embodiments, the method further includes administering a chemical adipolysis formulation into the tongue. The chemical adipolysis formulation, in some embodiments, comprises at least one compound selected from the group consisting of: phosphatidylcholine (PC), sodium deoxycholate (DOC), and deoxycholic acid (DC) (e.g., deoxycholate, cholanoic acid, and 3α, 12 α-dihydroxy-5β-cholanate).

In some embodiments, the method further includes administering a vasoconstriction agent (e.g., epinephrine) to the tongue.

In another aspect, the present disclosure describes a method for causing cryolysis of adipose tissue of a human oropharynx to treat apnea. The method includes administering a chemical adipolysis formulation into the oropharynx. The chemical adipolysis formulation, in some embodiments, is injected into the tongue (e.g., at a depth between about 1 and 5 cm).

In some embodiments, the chemical adipolysis formulation is injected into the uvula/palate. In some embodiments, the chemical adipolysis formulation is injected into the pharyngeal fat pads.

In some embodiments, the chemical adipolysis formulation comprises phosphatidylcholine (PC) having a concentration between about 0.1 and 1.0 mg/ml (e.g., at about 0.5 mg/ml).

In some embodiments, the chemical adipolysis formulation comprises sodium deoxycholate (DOC) having a concentration between about 0.1 and 1.0 mg/ml (e.g., at about 0.21 mg/ml).

In some embodiments, the method further includes causing cryolysis of adipose tissue of a human tongue. The method comprises (i) applying a heat exchanger so as to contact a portion of the dorsal surface of the tongue and a portion of the base of a tongue and (ii) circulating a heat-transfer fluid through the heat exchanger (e.g., to maintain the contact surface of the heat exchange at a temperature between −15° C. and 0° C.) (e.g., for a pre-defined treatment time, e.g., between 2 minutes and 2 hours). The heat exchanger, in some embodiments, includes a body having a first region and a second region for contacting the tongue. The first region, in some embodiments, has a contact surface (e.g., wherein the contact surface is curved or substantially flat) to contact a portion of the dorsal surface of the tongue. The second region, in some embodiments, forms a protrusion that extends from the first region and curves over and around the tongue to contact the base of the tongue.

In some embodiments, the step of causing cryolysis of adipose tissue of a human tongue further includes constricting the tongue in a manner to create a pressure thereon, whereby the dorsal surface and lateral surface of the tongue is confined by the constriction.

DETAILED DESCRIPTION

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intra-arterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Animal": As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

"Approximately": As used herein, the term "approximately" and "about" is intended to encompass normal statistical variation as would be understood by those of ordinary skill in the art as appropriate to the relevant context. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would 15 exceed 100% of a possible value).

"Biologically active": As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

"Human": In some embodiments, a human is an embryo, a fetus, an infant, a child, a teenager, an adult, or a senior citizen.

"Patient": As used herein, the term "patient" refers to a human or any non-human animal (e.g., mouse, rat, rabbit, dog, cat, cattle, swine, sheep, horse or primate) to whom therapy is administered. In many embodiments, a patient is a human being. In some embodiments, a patient is a human presenting to a medical provider for diagnosis or treatment of a disease, disorder or condition. In some embodiments, a patient displays one or more symptoms or characteristics of a disease, disorder or condition. In some embodiments, a patient does not display any symptom or characteristic of a disease, disorder, or condition. In some embodiments, a patient is someone with one or more features characteristic of susceptibility to or risk of a disease, disorder, or condition.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Symptoms are reduced": According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

"Treatment": As used herein, the term "treatment" (also "treat" or "treating") refers to any administration of a substance or application of a medical device that partially or completely alleviates, ameliorates, relives, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Figure 1:
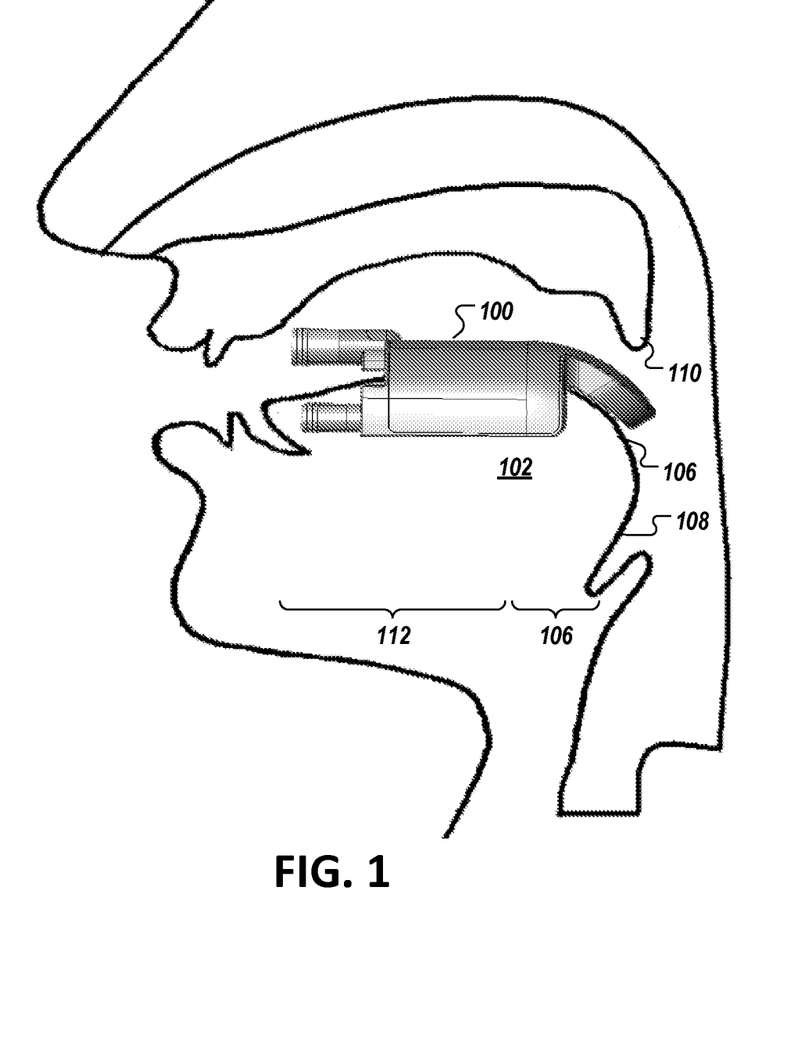
FIG. 1 is a diagram depicting a side cross-sectional view of a head of a human patient with a heat exchanger placed on the tongue to treat apnea.
Figure 2:
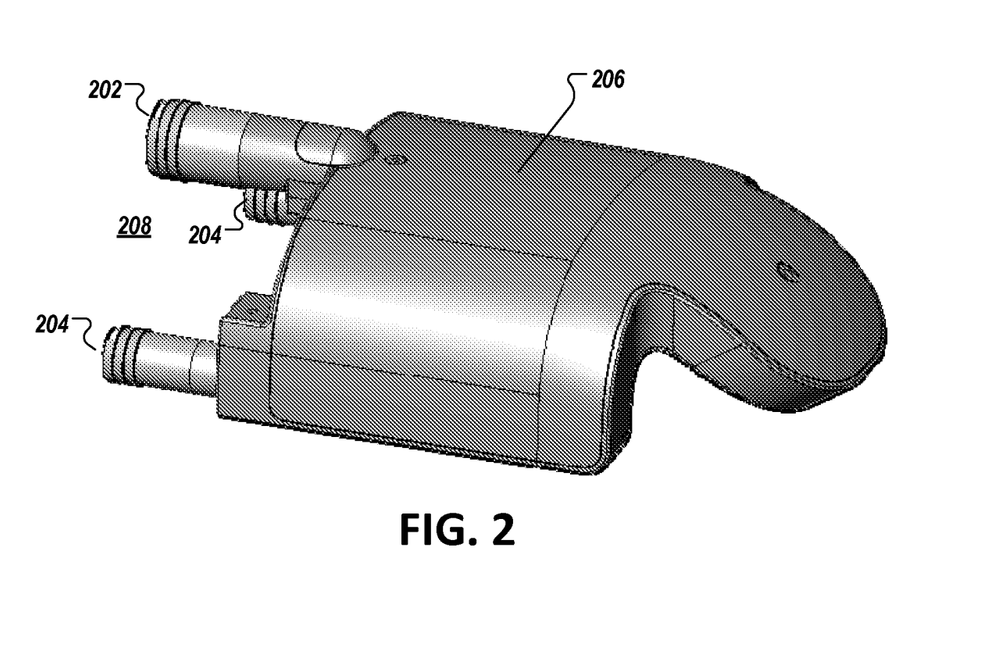
FIG. 2 is a diagram showing a perspective view of a heat exchanger for causing cryolysis of adipose tissue of a tongue (e.g., that of a human), according to an illustrative embodiment.
Figure 3:
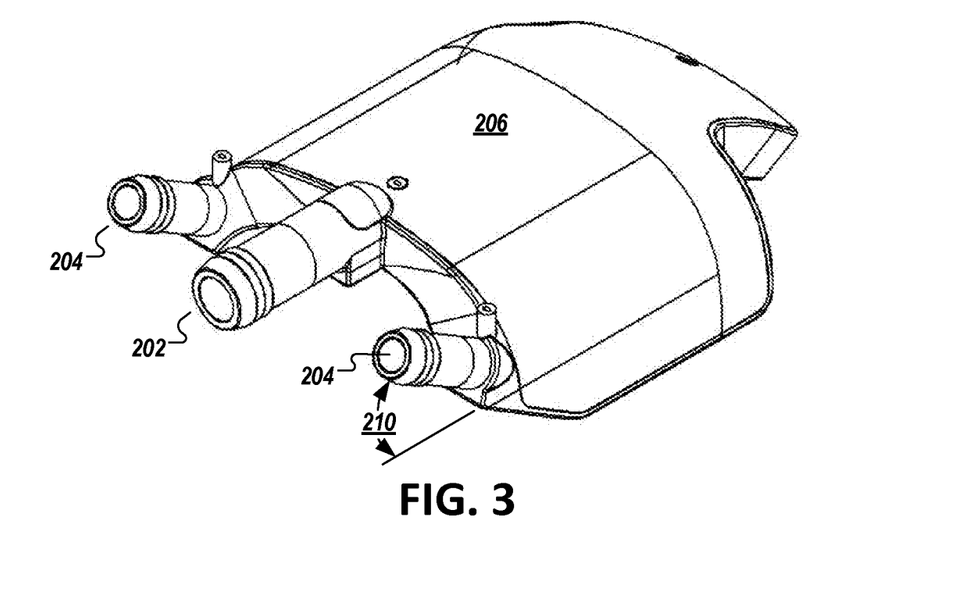
FIG. 3 is a diagram showing another perspective view of the heat exchanger of FIG. 2, according to another illustrative embodiment.

FIG. 1 is a diagram depicting a side cross-sectional view of a head of a human patient with a heat exchanger 100 placed on the tongue 102 to treat apnea according to an embodiment. FIG. 2 is a diagram showing a perspective view of the heat exchanger 100, for example, as that shown in FIG. 1, according to an embodiment. FIG. 3 is a diagram showing a perspective view of another heat exchanger 100, according to another illustrative embodiment.

The heat exchangers 100 includes a cooling inlet 202, a cooling outlet 204, and a body 206 having one or more channels 208 (not shown—see FIGS. 8 and 9) for circulating a heat-transfer fluid therein (e.g., chilled water, refrigerant, and/or water-glycerin solution). The one or more channels 208 connects the cooling inlet 202 and cooling outlet 204. In some embodiments, the body 206 comprises a material selected from the group consisting of copper, silver, and aluminum.

The cooling inlet 202 and the cooling outlet 204, in some embodiments, are located at a distal end 208 of the body 206. In some embodiments, the body 206 includes one or more cooling inlets 202 and one or more cooling outlets 204. In some embodiments, each of the cooling inlet 202 and the cooling outlet 204 includes a quick-disconnect fitting.

In some embodiments, at least one of the cooling inlet 202 and the cooling outlet 204 is angled with respect to the body

206. In FIG. 3, for example, the cooling outlet 204 is shown angled with respect to the body 206, for example, to allow the heat exchanger 100 to be placed in a compact manner within the oral cavity. The angle 210, in some implementations, are between about 5 and 60 degrees.

Figure 4:
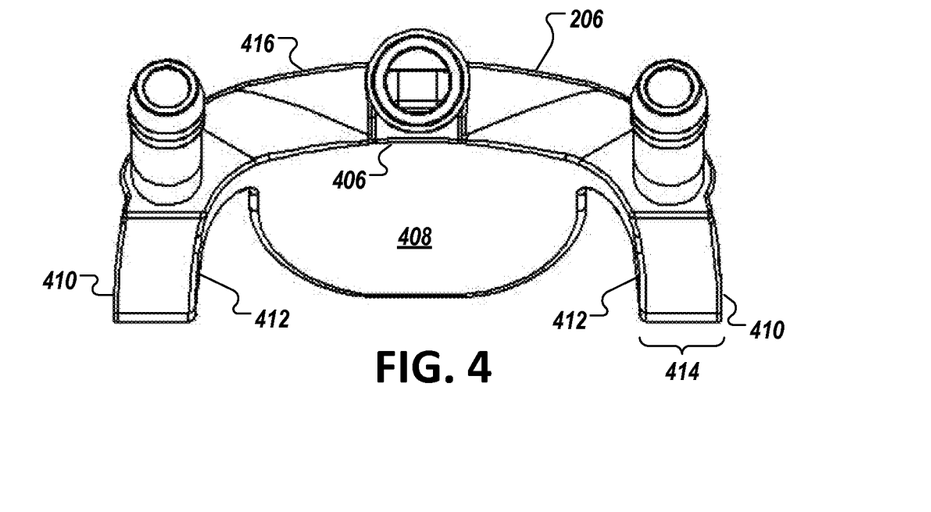
FIG. 4 is a diagram showing a front view of the heat exchanger, according to an illustrative embodiment.
Figure 5:
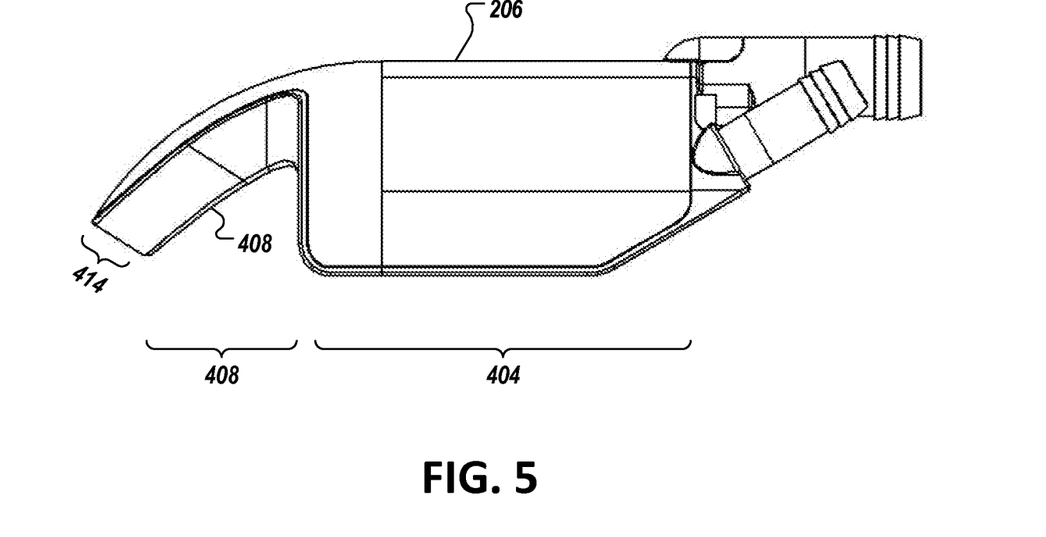
FIG. 5 is a diagram showing a side view of the heat exchanger, according to an illustrative embodiment.

FIGS. 4 and 5 are diagrams showing a front and a side view of the heat exchanger 100. The body 206, in some implementations, forms a contact surface to cover the base 106 (see FIG. 1) of the tongue 102. The base 106 of the tongue 102 refers to a portion of the oropharynx (which is composed of the base of the tongue 102, the pharyngeal wall 108, and the soft palate/uvula 110). The base 106 of the tongue 102 is located at the back-third region of the tongue and having the oropharyngeal tissue. The base 106 of tongue 102 is bounded anteriorly by the circumvallate papillae, laterally by the glossotonsillar sulci, and posteriorly by the epiglottis. The vallecula is a strip of mucosa that is the transition from the base 102 of the tongue 106 to the epiglottis; it is considered part of the base of tongue. The musculature of the base 106 of tongue 102 is contiguous with that of the oral tongue 112.

The top-side exterior surface 416 of the body 206, in some implementations, are curved to correspond to the interior surface of the oral cavity.

The body 206, in some implementations, includes (i) a first region 404 having a contact surface 406 (e.g., wherein the contact surface 406 (see also FIG. 6) is curved or substantially flat) to contact a portion of the dorsal surface of the tongue 102 and (ii) a second region 408 formed to contact a portion of the base 106 of the tongue 102. The second region 408 forms a protrusion that extends from the first region 404 and curves over and around the tongue 102 to contact the base 106 of the tongue 102. In some embodiments, the second region 408 is between about 1 and 2 inches in length. In other embodiments, the second region 408 is between about 0.5 inches and 1 inch in length.

The heat exchanger 100, in some implementations, includes a pair of side walls 410 that extends from the body 206 and forms a pair of side contact surfaces 412. The side walls 412 are dimensioned so that they contact the dorsal and lateral surfaces of the tongue in a manner so as to constrict the tongue 102 when the contact surface (e.g., 406, 408) is in contact with the tongue 102.

In some embodiments, the first region 404 and the second region 408 are of substantially the same thickness 414 (e.g., less than 10% difference). In some embodiments, the thickness 414 is between about 0.1 inches and 0.5 inches, even more preferably between 0.3 and 0.35 inches, and even more preferably at about 0.32 inches.

In some embodiments, the contact surface (e.g., 406, 408, 412) includes one or more concave recesses, whereby the recesses create a suction force between the interior surface of the concave recess and the corresponding surface of the base of the tongue when the contact surface is in contact with the base of the tongue. In some embodiments, the contact surface is concave (e.g., C-shaped, U-shaped, or V-shaped). The suction allows the heat exchanger 100 to tightly adhere to the tongue 102.

Figure 6:
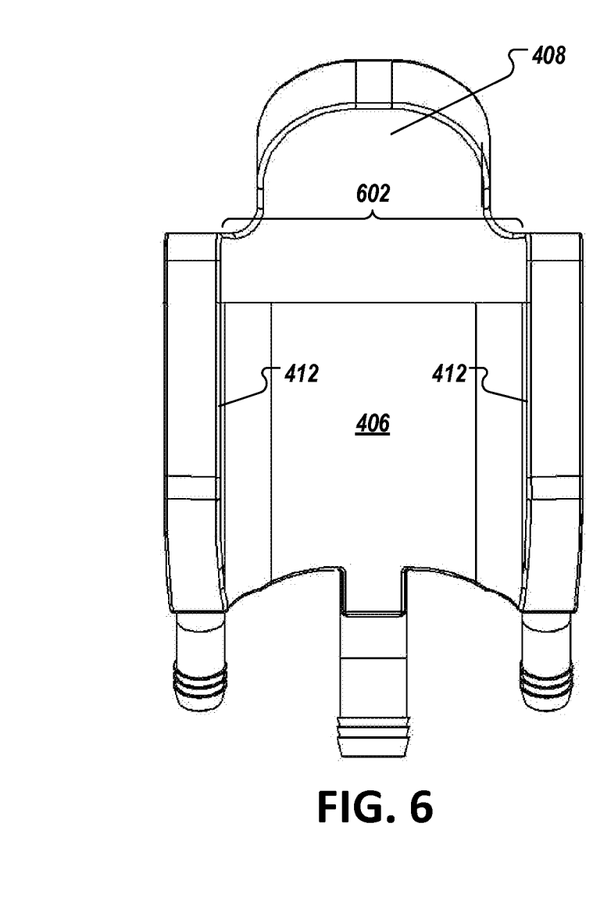
FIG. 6 is a diagram showing a bottom view of the heat exchanger, according to an illustrative embodiment.
Figure 7:
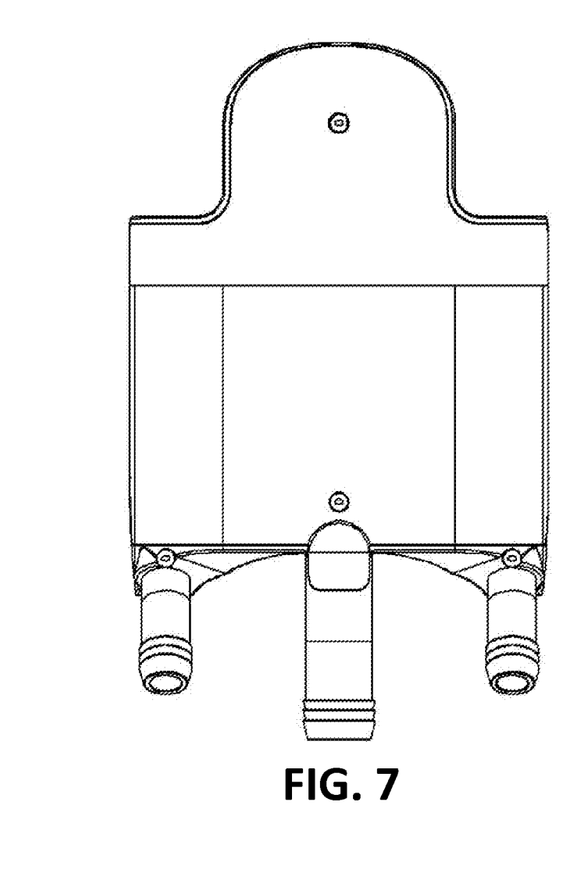
FIG. 7 is a diagram showing a top view of the heat exchanger, according to an illustrative embodiment.

FIGS. 6 and 7 are diagrams showing a bottom view and a top view of the heat exchanger 100. In some embodiments, the pair of side walls 412 forms a gap 602. The gap 602, in some embodiments, is between about 1.5 and 2 inches. This gap 602 is designed to be smaller than the width of the tongue in a relaxed state. To this end, when the heat exchanger 100 is seated on the tongue 102, the tongue 102 is compressed between the pair of side walls 412. The compression of the tongue 102 by the side walls 412 creates a pressure in the tongue so as to reduce the blood flow within the tongue. As a result, the heat exchanger 100 can cool the tongue 102 to a temperature (e.g., to invoke a cryolytic tissue response that triggers the apoptosis process within the adipose tissue) with less application/exposure time and/or more elevated temperature than without the constriction.

Figure 8:
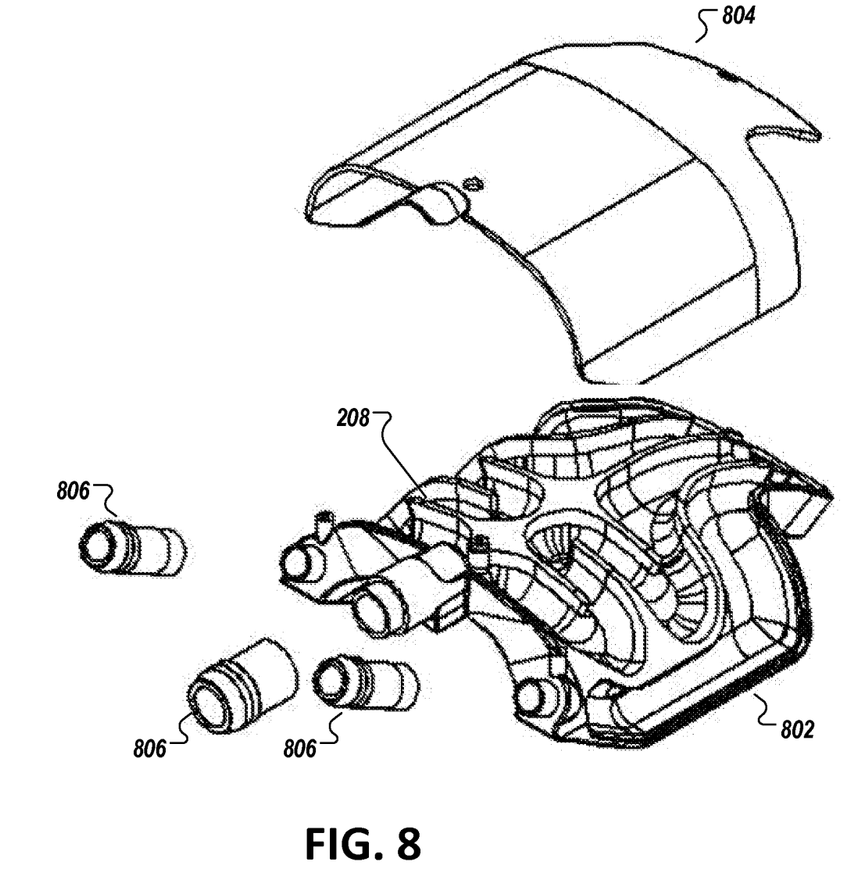
FIG. 8 is a diagram showing a disassembled view of the heat exchanger, according to an illustrative embodiment.
Figure 9:
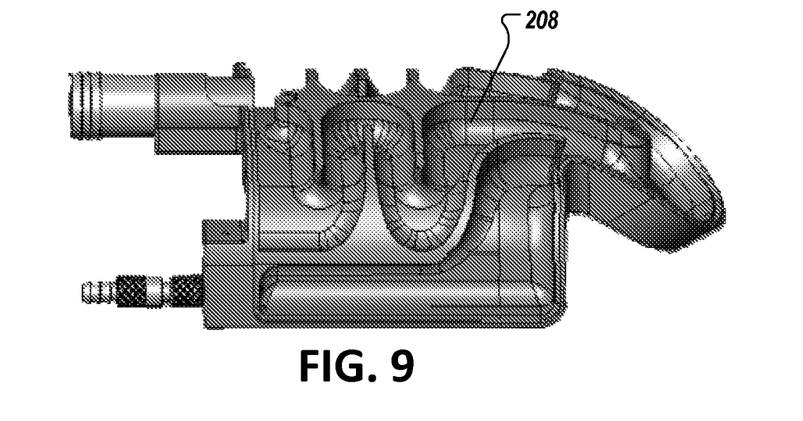
FIG. 9 is a diagram showing a side view of the interior of the heat exchanger, according to an illustrative embodiment.

FIG. 8 is a diagram showing a disassembled view of the heat exchanger. FIG. 9 is a diagram showing a side view of the interior of the heat exchanger. As shown in FIGS. 8 and 9, in some embodiments, the one or more channels form a serpentine pattern that span a substantial portion (e.g., greater than about 50%) of the interior of the body 206.

The body 206, in some implementations, include a main body portion 802 and a cover portion 804 that mates together to form the body 206.

In some embodiments, each of the cooling inlet 202 and the cooling outlet 204 includes a quick-disconnect fitting 806 to connect to a hose that is connected to a chilled-fluid source (for example, a fluid chilling and circulation system).

Figure 10:
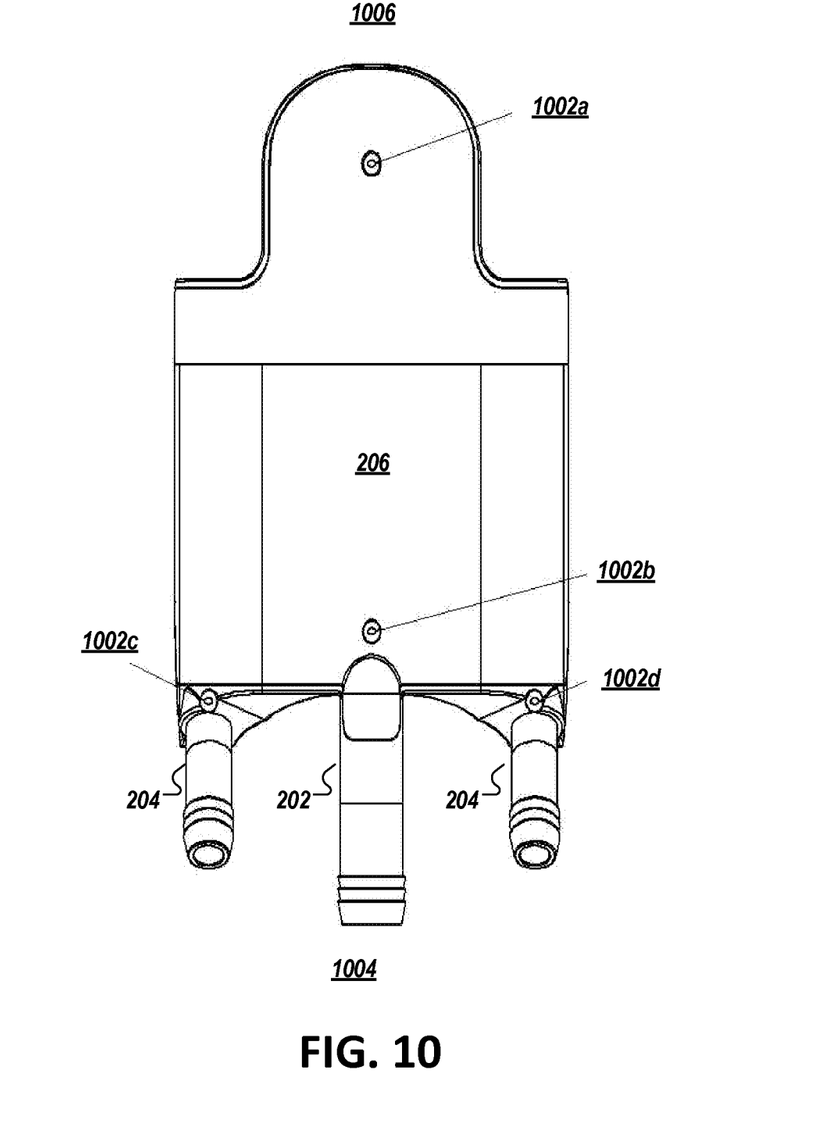
FIG. 10 is a diagram showing the heat exchanger with thermal sensors, according to an illustrative embodiment.

FIG. 10 is a diagram showing the heat exchanger 100 with thermal sensors 1002*a-d*. In some embodiments, the thermal sensors include one or more thermocouples, thermistors, resistance thermometers, and/or silicon band-gap temperature sensors.

The thermal sensors 1002, in some implementations are placed at a distal end 1004 of the contact surface of the body 206, the inlet 202, the outlet 204, and a proximal end 1006 of the contact surface of the body 206. The thermal sensors 1002 may be employed in a feedback loop to control, for example, the temperature of the heat transfer fluid being circulated within the heat exchanger or the flow rate of the heat transfer fluid.

As shown, the thermal sensor 1002*a* is placed on the contact surface of the second region 408 formed to contact a portion of the base 106 of the tongue 102.

Figure 11A:
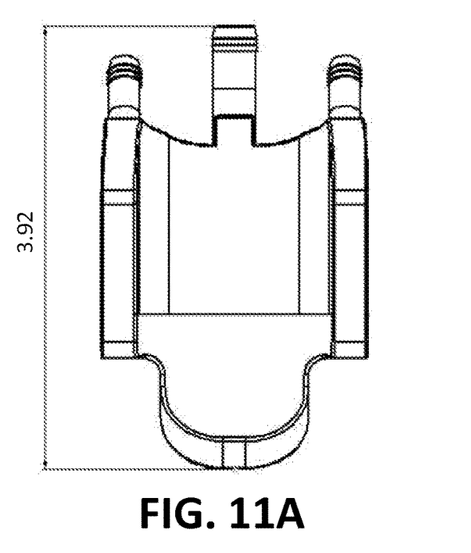
FIGS. 11A-C are diagrams of a heat exchanger, according to an illustrative embodiment.
Figures 11B, 11C:
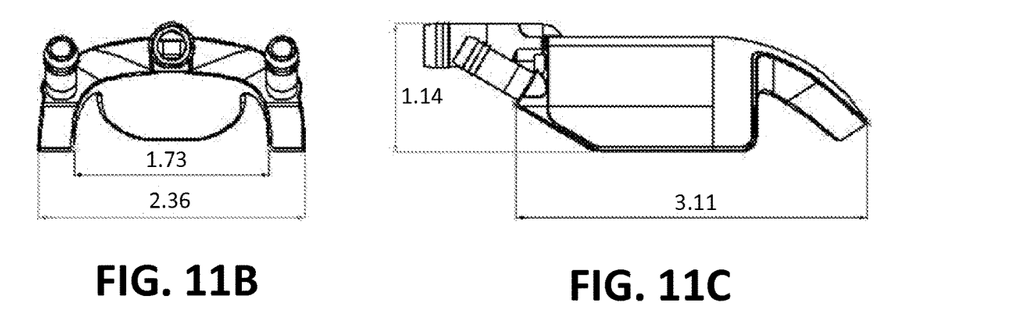

FIGS. 11A-C are diagrams of a heat exchanger. The figure illustrates some illustrative dimensions (shown in inches) for the heat exchanger. In some embodiments, the contact surface and the side contact surfaces have a combined surface area between about 4 and 10 square inches.

In some embodiments, the heat exchanger further includes a suction inlet located on the contact surface; a suction outlet having a coupling to couple to a hose; and a suction channel connecting the suction inlet and the suction outlet. The suction inlet, in some implementations, is located on the contact surface (e.g., 406, 408, and/or 412). The suction outlet, in some implementations, is located (i) at the distal end of the body and (ii) proximal to the cooling inlet and cooling outlet. The suction outlet may include a fitting to connect to a hose that connect to a vacuum system.

Figure 12:
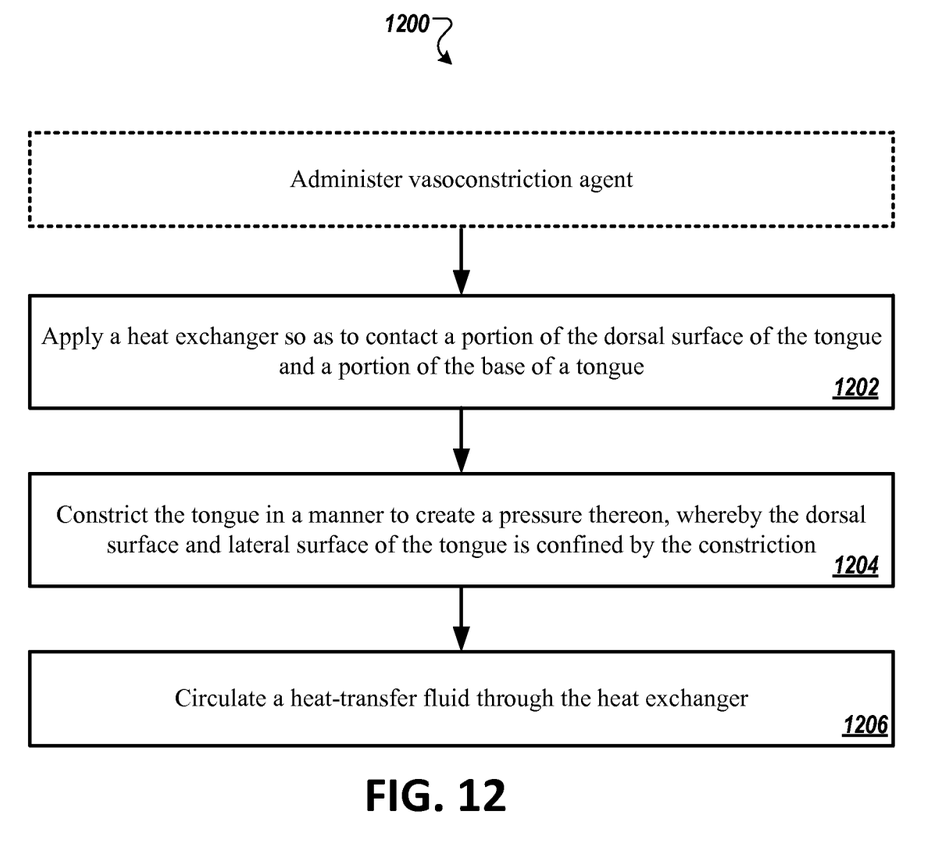
FIG. 12 is a flowchart illustrating a method for causing adipolysis of adipose tissue to treat apnea, according to an illustrative embodiment.

FIG. 12 is a flowchart illustrating a method 1200 for causing adipolysis of adipose tissue to treat apnea. The method 1200 includes applying a heat exchanger 100 so as to contact a portion of the dorsal surface of the tongue 102 and a portion of the base 106 (e.g., the oropharynx) of a tongue 102 (step 1202). The heat exchanger 100 includes a body 206 having a first region 404 and a second region 408 for contacting the tongue in which the first region 404 has a contact surface (e.g., wherein the contact surface is curved or substantially flat) to contact a portion of the dorsal surface of the tongue, and in which the second region 408 forms a protrusion that extends from the first region and curves over and around the tongue to contact the base 106 of the tongue 102.

The method 1200 further includes constricting the tongue in a manner to create a pressure thereon (step 1204), whereby the dorsal surface and lateral surface of the tongue is confined by the constriction.

The method further includes circulating a heat-transfer fluid through the heat exchanger (step 1206) (e.g., to maintain the contact surface of the heat exchange at a temperature between −15° C. and 0° C., preferably at −10° C.) (e.g., for a pre-defined treatment time, e.g., between 10 minutes and 2 hours).

In some embodiments, the method 1200 further includes administering a chemical adipolysis formulation into the tongue. The chemical adipolysis formulation, in some embodiments, comprises at least one compound selected from the group consisting of: phosphatidylcholine (PC), sodium deoxycholate (DOC), and deoxycholic acid (DC) (e.g., deoxycholate, cholanoic acid, and 3α, 12 α-dihydroxy-5β-cholanate).

The chemical adipolysis formulation may be administered (e.g., injected) to the tongue or treatment area prior to the heat exchanger being placed on the treatment area. Alternatively, the chemical adipolysis formulation may be administered to the tongue or treatment area after the cryolysis treatment with the heat exchanger has been performed and completed.

In some embodiments, a hand held transducer is employed prior the administration of the chemical adipolysis formulation to identity the and size of fat accumulation in the tongue, soft palate, and pharyngeal wall. Other imaging modality (e.g., ultrasound, MRI, PET, CT, X-Ray, among others) may be employed to identify the fat accumulation in the tongue for the purpose of administering the chemical adipolysis formulation.

In some embodiments, the method 1200 further includes administering a vasoconstriction agent (e.g., epinephrine) to the tongue 102. The vasoconstriction agent, once injected, reduces the flow of blood to and within the tongue, thereby allowing the subcutaneous tissue within the tongue to reach the intended treatment temperature, potentially, with less application time and/or more elevated chilled temperature as compared to no vasoconstriction agent being administered. In some embodiments, the vasoconstriction agent is employed to increase the depth of the treatment (i.e., the treatment effective range) by allowing the treatment temperature to reach deeper adipose tissue within the tongue.

In some embodiments, a chilled balloon may be employed in conjunction with the heat exchanger and/or vasoconstriction agent to concurrently treat one or more sites in the oropharynx (for example, the base of the tongue, the lateral pharyngeal wall, and/or the soft palate or uvula). The chilled balloon is selectively expandable between an expanded state and a deflated state and is configured to expand, in the expanded state, in the oropharynx to contact at least one of the pharyngeal wall and the palate (i.e., uvula).

Figure 13:
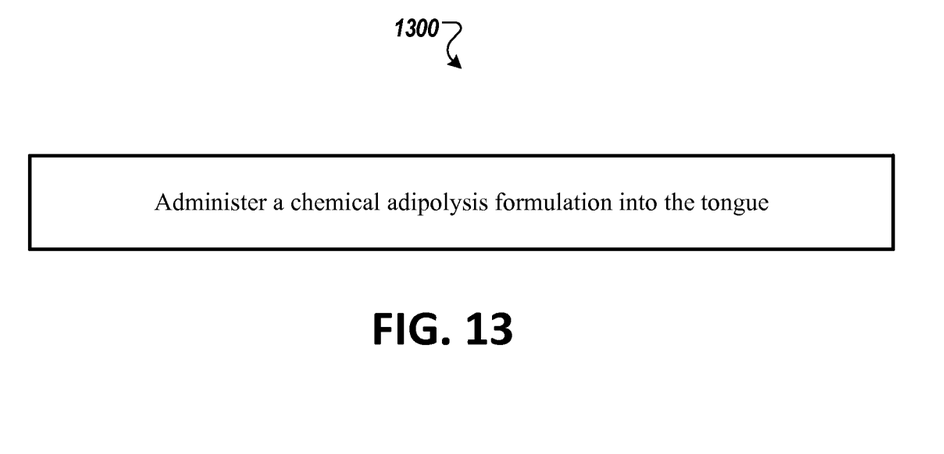
FIG. 13 is a flowchart illustrating a method for causing adipolysis of adipose tissue to treat apnea, according to an illustrative embodiment.

FIG. 13 is a flowchart illustrating a method 1300 for causing adipolysis of adipose tissue to treat apnea. The method 1300 includes administering a chemical adipolysis formulation into the oropharynx.

The chemical adipolysis formulation, in some embodiments, is injected into the tongue (e.g., at a depth between about 1 and 5 cm). Deeper injections are preferable, in some embodiments, to cool the deeper adipose tissue. In some embodiments, the chemical adipolysis formulation is injected into the uvula/palate.

In some embodiments, the chemical adipolysis formulation is injected into the pharyngeal fat pads. The lateral pharyngeal fat pads have been shown to contribute to sleep apnea. These fat pads are in proximity to vital nerves and the carotid artery making them very difficult to reduce surgically. The disclosed treatment provides a minimally invasive or noninvasive method of reducing the size of the lateral pharyngeal fat pad for the treatment of sleep apnea. Chemical lipolysis and cryolipolysis cause adipose cell death through different actions and may act synergistically. By combining the two methods, the concentration of the DOC and/or PC may be reduced. Also, the exposure time can be reduced and the temperature increased for the cryolipolysis treatment. Chemical lipolysis with or without cryolysis may be employed to reduce the size and volume of lateral pharyngeal fat pads.

The chemical adipolysis formulation, in some embodiments, comprises at least one compound selected from the group consisting of: phosphatidylcholine (PC), sodium deoxycholate (DOC), and deoxycholic acid (DC) (e.g., deoxycholate, cholanoic acid, and 3α, 12 α-dihydroxy-5β-cholanate).

In some embodiments, the chemical adipolysis formulation comprises phosphatidylcholine (PC) having a concentration between about 0.1 and 1.0 mg/ml (e.g., at about 0.5 mg/ml).

In some embodiments, the chemical adipolysis formulation comprises sodium deoxycholate (DOC) having a concentration between about 0.1 and 1.0 mg/ml (e.g., at about 0.21 mg/ml).

Deoxycholic acid (DC), also known as deoxycholate, cholanoic acid, and 3α, 12α-dihydroxy-5β-cholanate, is one of the secondary bile acids, which are metabolic byproducts of intestinal bacteria and is used by the human body to emulsify fat for absorption in the intestines. Sodium deoxycholate, the sodium salt of deoxycholic acid, is frequently used in mesotherapy injections, mixed with phosphatidylcholine.

Without wishing to be bound to a particular theory, the action of Deoxycholic acid (DC) is to destabilize cell membranes. DC activity is neutralized by binding of DC binding proteins on the surface of most cell types. Adipocytes lack sufficient DC binding proteins to minimize the destabilization, thus adipocytes are selected from cell death.

Phosphatidylcholines are a class of phospholipids that have also been shown to cause lipolysis when injected. Phosphatidylcholine formulation may be used to dissolve local fat deposits.

These agents may be used in conjunction with cryolipolysis to increase adipocyte apoptosis and cell death. These agents can be used individually or together with other agents. These agents can also be used independently or together with the heat exchanger, described herein.

These agents, individually or in combination, may be injected into other areas of oropharyngeal fat that may be contributing to sleep apnea, specifically the soft palate/uvula and the lateral pharyngeal fat pads.

In some embodiments, the method 1300 further includes causing cryolysis of adipose tissue of a human tongue. The method 1300 comprises (i) applying a heat exchanger 100 so as to contact a portion of the dorsal surface of the tongue 102 and a portion of the base 106 of a tongue 102 and (ii) circulating a heat-transfer fluid through the heat exchanger 102 (e.g., to maintain the contact surface of the heat exchange at a temperature between −15° C. and 0° C.) (e.g., for a pre-defined treatment time, e.g., between 2 minutes and 2 hours). The heat exchanger 100, in some embodiments, includes a body 206 having a first region 404 and a second region 408 for contacting the tongue 102. The first region 404, in some embodiments, has a contact surface (e.g., wherein the contact surface is curved or substantially flat) to contact a portion of the dorsal surface of the tongue. The second region 408, in some embodiments, forms a protrusion that extends from the first region 404 and curves over and around the tongue 102 to contact the base 106 of the tongue 102.

In some embodiments, the step of causing cryolysis of adipose tissue of a human tongue further includes constricting the tongue in a manner to create a pressure thereon, whereby the dorsal surface and lateral surface of the tongue is confined by the constriction.

Methods disclosed herein contemplate application, adaptation, or use of information and embodiments described in U.S. patent application Ser. No. 13/359,000, which was filed on Jan. 26, 2012 entitled "Apparatus and Methods for Treatment of Obstructive Sleep Apnea Utilizing Cryolysis of Adipose Tissues" and published as US 2012/197361 A1 on Aug. 2, 2012, the entire contents of which are hereby incorporated by reference in its entirety herein.

What is claimed is:

1. A heat exchanger for causing cryolysis of adipose tissue of a human tongue, the heat exchanger comprising:
    a cooling inlet;
    a cooling outlet;
    a body having one or more channels for circulating a heat-transfer fluid therein, the one or more channels connecting the cooling inlet and the cooling outlet, wherein the body comprises (i) a first region having a first contact surface configured to contact a portion of a dorsal surface of the tongue and (ii) a second region having a second contact surface configured to contact a portion of a base of the tongue, the second region extending from the first region; and
    a pair of side walls extending from the body and forming a pair of side contact surfaces,
    wherein the pair of side walls are dimensioned so that they contact the dorsal and lateral surfaces of the tongue in a manner so as to constrict the tongue when the first and second contact surfaces are in contact with the tongue.

2. The heat exchanger of claim 1, wherein at least one of the first contact surface, the second contact surface, and the pair of side contact surfaces comprises one or more concave recesses, whereby the one or more concave recesses are configured to create a suction force between the interior surface of the one or more concave recesses and a corresponding surface of the tongue when the heat exchanger is in contact with the tongue.

3. The heat exchanger of claim 1, wherein the first region and the second region are of substantially the same thickness.

4. The heat exchanger of claim 1, wherein the second region is between about 1 and 2 inches in length.

5. The heat exchanger of claim 1, wherein the pair of side walls forms a gap therebetween, the gap being between about 1.5 and 2 inches.

6. The heat exchanger of claim 1, wherein the one or more channels form a serpentine pattern that span a substantial portion of an interior of the body.

7. The heat exchanger of claim 1, wherein the cooling inlet and the cooling outlet are located at a distal end of the body.

8. The heat exchanger of claim 1, wherein each of the cooling inlet and the cooling outlet comprises a quick-disconnect fitting.

9. The heat exchanger of claim 1, wherein at least one of the cooling inlet and the cooling outlet is angled with respect to the body.

10. The heat exchanger of claim 1 further comprising:
    a suction inlet located on at least one of the first contact surface, the second contact surface, and the pair of side contact surfaces;
    a suction outlet having a coupling to couple to a hose; and
    a suction channel connecting the suction inlet and the suction outlet.

11. The heat exchanger of claim 10, wherein the suction outlet is located (i) at a distal end of the body and (ii) proximal to the cooling inlet and the cooling outlet.

12. The heat exchanger of claim 1, further comprising:
    one or more thermal sensors, wherein
    at least one of the one or more thermal sensors is located at a location selected from the group consisting of a distal end of the first contact surface or the second contact surface of the body, the cooling inlet, the cooling outlet, and a proximal end of the first contact surface or the second contact surface of the body.

13. The heat exchanger of claim 1, wherein the first contact surface, the second contact surface, and the pair of side contact surfaces have a combined surface area between about 4 and 10 square inches.

14. The heat exchanger of claim 1, wherein the first contact surface is concave.

15. The heat exchanger of claim 1, wherein the body comprises a material selected from the group consisting of copper, silver, and aluminum.

16. The heat exchanger of claim 1, wherein the body comprises a top-side exterior surface, said top-side exterior surface being curved to correspond to an oral cavity surface.

17. A method for causing adipolysis of adipose tissue of a human tongue to treat apnea, the method comprising:
    applying a contact surface of a heat exchanger so as to contact a portion of a dorsal surface of the tongue and a portion of a base of the tongue;
    constricting dorsal and lateral surfaces of the tongue; and
    circulating a heat-transfer fluid through the heat exchanger to maintain the contact surface of the heat exchanger at a temperature between $-15°$ C. and $0°$ C. for a pre-defined treatment time between 10 minutes and 2 hours.

18. The method of claim 17 further comprising:
    administering a chemical adipolysis formulation into the tongue.

19. The method of claim 18, wherein the chemical adipolysis formulation comprises at least one compound selected from the group consisting of: phosphatidylcholine (PC), sodium deoxycholate (DOC), and deoxycholic acids (DC) like deoxycholate, cholanoic acid, and 3α, 12 α-dihydroxy-5β-cholanate.

20. The method of claim 17 further comprising:
    administering a vasoconstriction agent to the tongue.

21. The method of claim 17, wherein the heat exchanger further comprises a body and one or more channels in an interior of the body, the contact surface being disposed on the body, the circulating step comprising circulating heat-transfer fluid through the one or more channels.

22. The method of claim 21, wherein the heat exchanger further comprises a pair of side walls extending from the body, the constricting step comprising constricting the dorsal and lateral surfaces of the tongue with the pair of side walls.

23. The method of claim 21, wherein the one or more channels are disposed in a serpentine pattern.

24. The method of claim 17, further comprising applying suction between the heat exchanger and the tongue.

25. The method of claim 17, further comprising sensing a temperature of the contact surface and controlling a temperature or flow rate of the heat-transfer fluid.

26. The method of claim 17, wherein the heat exchanger comprises a cooling inlet and a cooling outlet, the circulating step comprising circulating the heat-transfer fluid through the heat exchanger from the cooling inlet to the cooling outlet, the method further comprising sensing a temperature at the cooling inlet or the cooling outlet and controlling a temperature or flow rate of the heat-transfer fluid.

* * * * *